(12) United States Patent
Slazas et al.

(10) Patent No.: US 10,603,157 B2
(45) Date of Patent: *Mar. 31, 2020

(54) BRAID IMPLANT DELIVERY AND RETRACTION DEVICE WITH DISTAL ENGAGEMENT

(71) Applicant: DePuy Synthes Products, Inc., Raynham, MA (US)

(72) Inventors: Robert Slazas, Raynham, MA (US); Juan Lorenzo, Raynham, MA (US); Lacey Gorochow, Raynham, MA (US); Pedro Pedroso, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/056,038

(22) Filed: Aug. 6, 2018

(65) Prior Publication Data

US 2019/0110882 A1 Apr. 18, 2019

Related U.S. Application Data

(63) Continuation-in-part of application No. 13/802,114, filed on Mar. 13, 2013.

(51) Int. Cl.
*A61F 2/966* (2013.01)
*A61F 2/07* (2013.01)
(Continued)

(52) U.S. Cl.
CPC ............... *A61F 2/07* (2013.01); *A61F 2/844* (2013.01); *A61F 2/848* (2013.01); *A61F 2/88* (2013.01);
(Continued)

(58) Field of Classification Search
CPC .. A61F 2/848; A61F 2/95; A61F 2/962; A61F 2/966; A61F 2002/8486; A61F 2002/9528; A61F 2002/9534
See application file for complete search history.

(56) References Cited

U.S. PATENT DOCUMENTS 5,282,824 A 2/1994 Gianturco
5,387,235 A 2/1995 Chuter
(Continued)

FOREIGN PATENT DOCUMENTS

EP 0701800 A1 3/1996
EP D 701 800 A1 3/1996
(Continued)

OTHER PUBLICATIONS

Partial European Search Report dated Feb. 13, 2018 during the prosecution of European Patent Application 17194063.8.
(Continued)

*Primary Examiner* — Ryan J. Severson
(74) *Attorney, Agent, or Firm* — Troutman Sanders LLP

(57) ABSTRACT

A braid implant delivery and retraction device having a catheter, an expandable element and a delivery wire with distal, pusher, and recapture bumps. The expandable element having compressed, partially delivered, and implanted configurations. Delivering the braid can include engaging the distal bump till the braid is in the partially delivered configuration. If the user needs to recapture the braid, the recapture bump engages the braid proximally. To fully implant the braid, the distal bump is used until the braid is partially delivered and the distal bump disengages, now the pusher bump completes implanting by proximally pushing the braid completely out of the catheter.

19 Claims, 12 Drawing Sheets

(51) Int. Cl.
*A61F 2/844* (2013.01)
*A61F 2/92* (2013.01)
*A61F 2/95* (2013.01)
*A61F 2/88* (2006.01)
*A61F 2/848* (2013.01)
*A61F 2/90* (2013.01)
*A61F 2/82* (2013.01)

(52) U.S. Cl.
CPC ................. *A61F 2/90* (2013.01); *A61F 2/92* (2013.01); *A61F 2/95* (2013.01); *A61F 2/966* (2013.01); *A61F 2002/823* (2013.01); *A61F 2002/8486* (2013.01); *A61F 2002/9522* (2013.01); *A61F 2002/9534* (2013.01); *A61F 2002/9665* (2013.01)

(56) References Cited

U.S. PATENT DOCUMENTS

| | | |
|---|---|---|
| 5,702,418 A | 12/1997 | Ravenscroft |
| 5,961,546 A | 10/1999 | Robinson et al. |
| 6,015,432 A | 1/2000 | Rakos et al. |
| 6,123,723 A | 9/2000 | Konya et al. |
| 6,168,621 B1 | 1/2001 | Vrba |
| 6,264,683 B1 | 7/2001 | Stack et al. |
| 6,280,465 B1 | 8/2001 | Cryer |
| 6,409,755 B1 | 6/2002 | Vrba |
| 6,612,012 B2 | 9/2003 | Mitelberg et al. |
| 6,673,106 B2 | 1/2004 | Mitelberg et al. |
| 6,740,113 B2 | 5/2004 | Vrba |
| 6,818,013 B2 | 11/2004 | Mitelberg et al. |
| 6,833,003 B2 | 12/2004 | Jones et al. |
| 6,945,994 B2 | 9/2005 | Austin et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 7,001,422 B2 | 2/2006 | Escamilla et al. |
| 7,037,331 B2 | 5/2006 | Mitelberg et al. |
| 7,201,769 B2 | 4/2007 | Jones et al. |
| 7,309,351 B2 | 12/2007 | Escamilla et al. |
| 7,628,806 B2 | 12/2009 | Yampolsky et al. |
| 7,655,031 B2 * | 2/2010 | Tenne .................. A61F 2/95 623/1.11 |
| 8,043,353 B2 | 10/2011 | Kaufmann et al. |
| 8,092,510 B2 | 1/2012 | Metcalf et al. |
| 8,182,523 B2 * | 5/2012 | Tenne .................. A61F 2/95 623/1.11 |
| 8,597,276 B2 | 12/2013 | Vongphakdy et al. |
| 8,641,748 B2 | 2/2014 | Hebert et al. |
| 8,816,247 B1 | 8/2014 | Janardhan et al. |
| 8,864,811 B2 * | 10/2014 | Kao .................. A61F 2/95 623/1.11 |
| 9,301,864 B2 * | 4/2016 | Kao .................. A61F 2/966 |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2005/0049668 A1 | 3/2005 | Jones et al. |
| 2005/0049669 A1 | 3/2005 | Jones et al. |
| 2005/0257674 A1 | 11/2005 | Nishri et al. |
| 2007/0233224 A1 | 10/2007 | Leynov |
| 2007/0255385 A1 | 11/2007 | Tenne et al. |
| 2008/0071307 A1 | 3/2008 | DeBruyne et al. |
| 2009/0306761 A1 | 12/2009 | Hebert et al. |
| 2011/0264186 A1 | 10/2011 | Berlung et al. |
| 2011/0307049 A1 | 12/2011 | Kao |
| 2014/0200648 A1 | 7/2014 | Newell et al. |
| 2014/0277332 A1 * | 9/2014 | Slazas .................. A61F 2/82 623/1.11 |
| 2014/0277360 A1 | 9/2014 | Gimary et al. |
| 2016/0058524 A1 | 3/2016 | Tehrani et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |

(56) References Cited

U.S. PATENT DOCUMENTS

| | | |
|---|---|---|
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0092766 A1* | 4/2018 | Gorochow .............. A61F 2/844 |
| 2018/0263794 A1* | 9/2018 | Slazas ...................... A61F 2/82 |

FOREIGN PATENT DOCUMENTS

| | | |
|---|---|---|
| EP | 2777638 A1 | 9/2014 |
| EP | 2777649 A1 | 9/2014 |
| FR | 2939637 A1 | 6/2010 |
| JP | 3-503246 A | 7/1991 |
| JP | 11-57010 A | 3/1999 |
| JP | 3-503246 B2 | 3/2004 |
| JP | 2004-267750 A | 9/2004 |
| WO | 1989008433 A1 | 9/1989 |
| WO | 9943379 A1 | 9/1999 |
| WO | 2008130530 A1 | 10/2008 |
| WO | 2012/096687 A1 | 7/2012 |
| WO | 2013126299 A1 | 8/2013 |

OTHER PUBLICATIONS

Notification of Reasons for Refusal issued in corresponding Japanese Patent Application No. 2014-048609 dated Nov. 21, 2017 (English translation only).

Examination report No. 1 for standard patent application issued in corresponding Australian Patent Application No. 2014201193 dated Oct. 13, 2017.

European Application No. 14159541.3 Search Report dated Aug. 4, 2014.

State Intellectual Property Office of People's Republic China issued in corresponding Chinese Patent Application No. 201410091651.6 (English translation only).

Extended European Search Report issued in corresponding European Patent Application No. 16 19 0078 dated Jan. 3, 2020.

\* cited by examiner

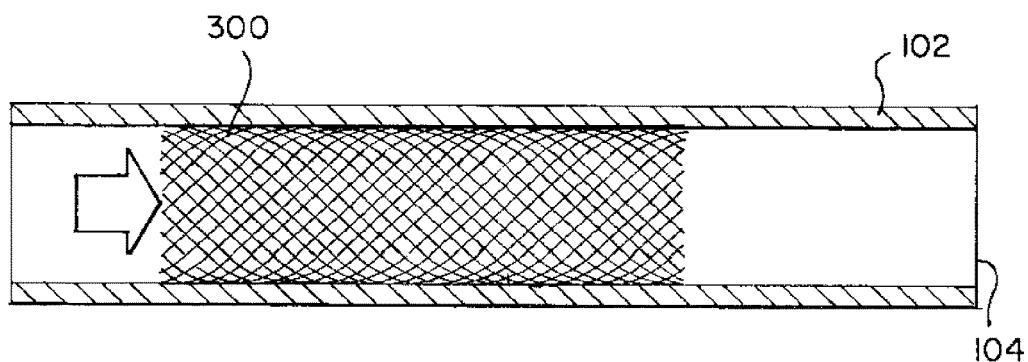
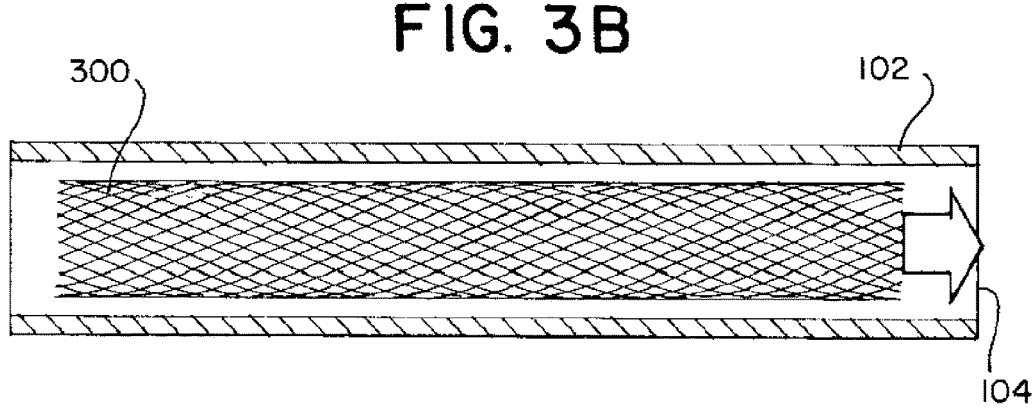
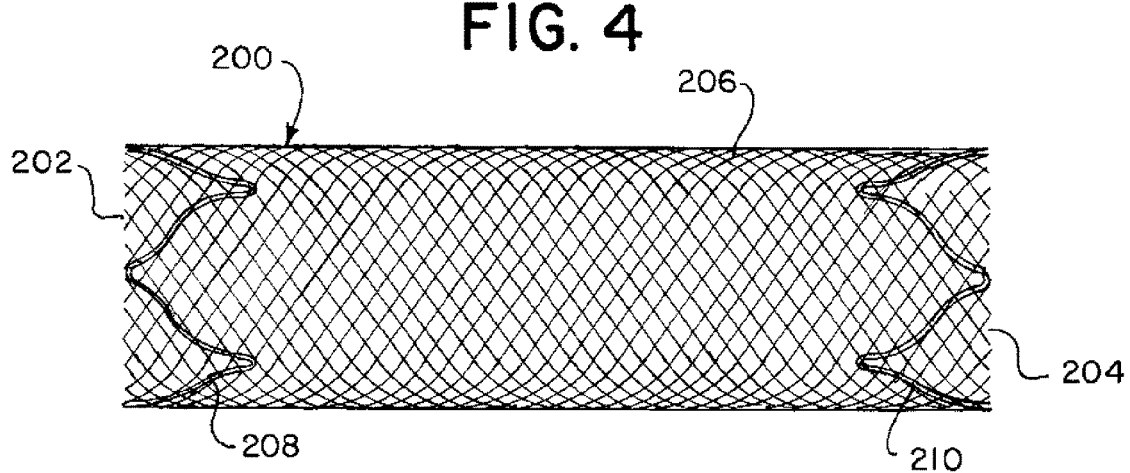

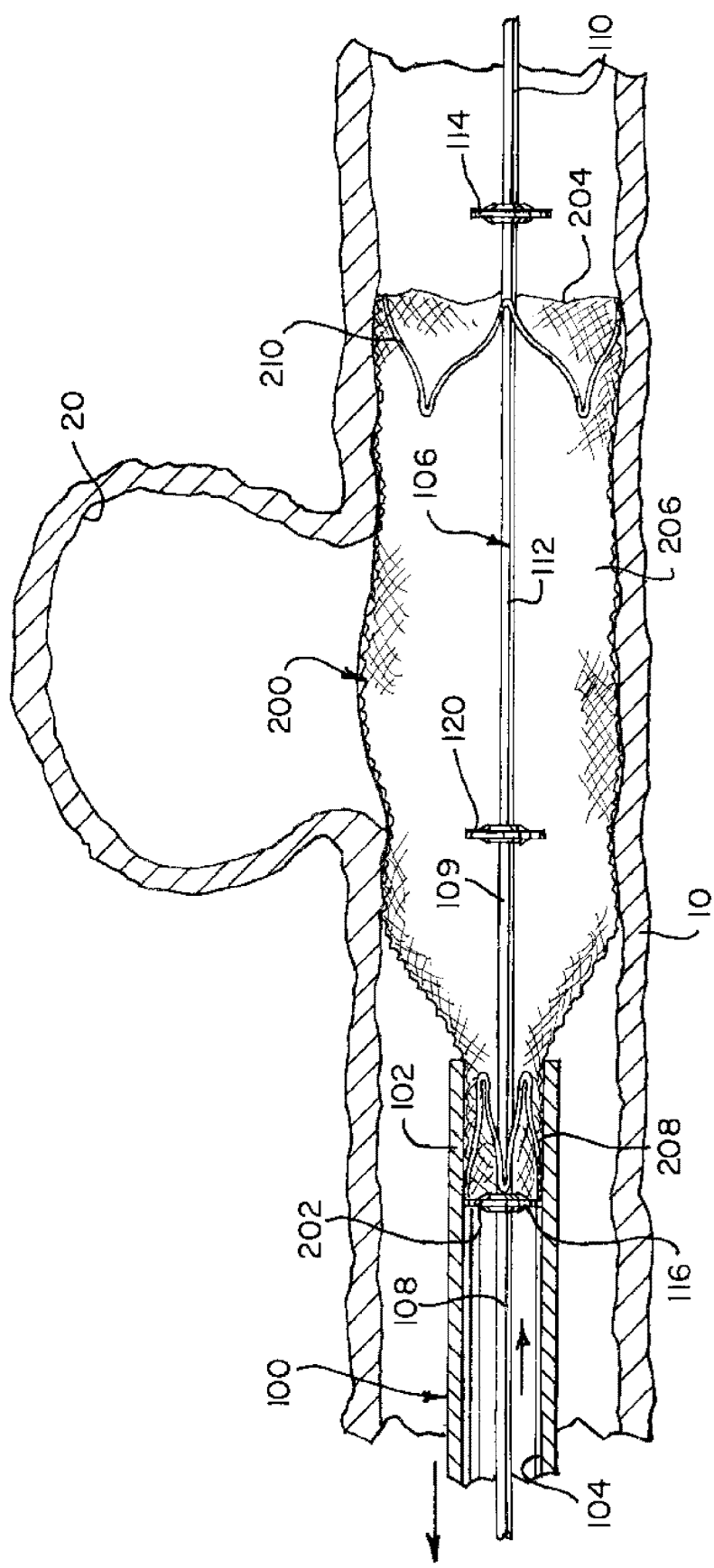

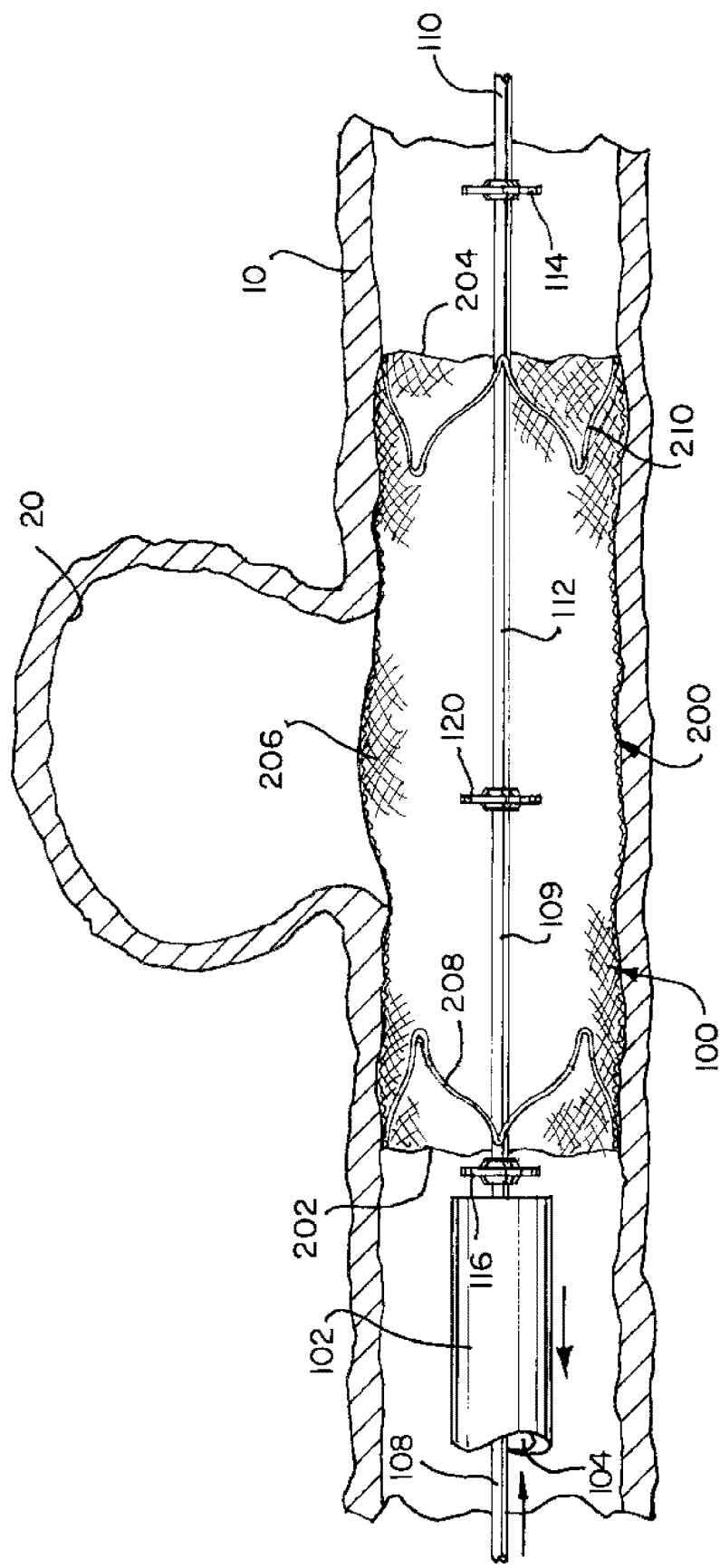

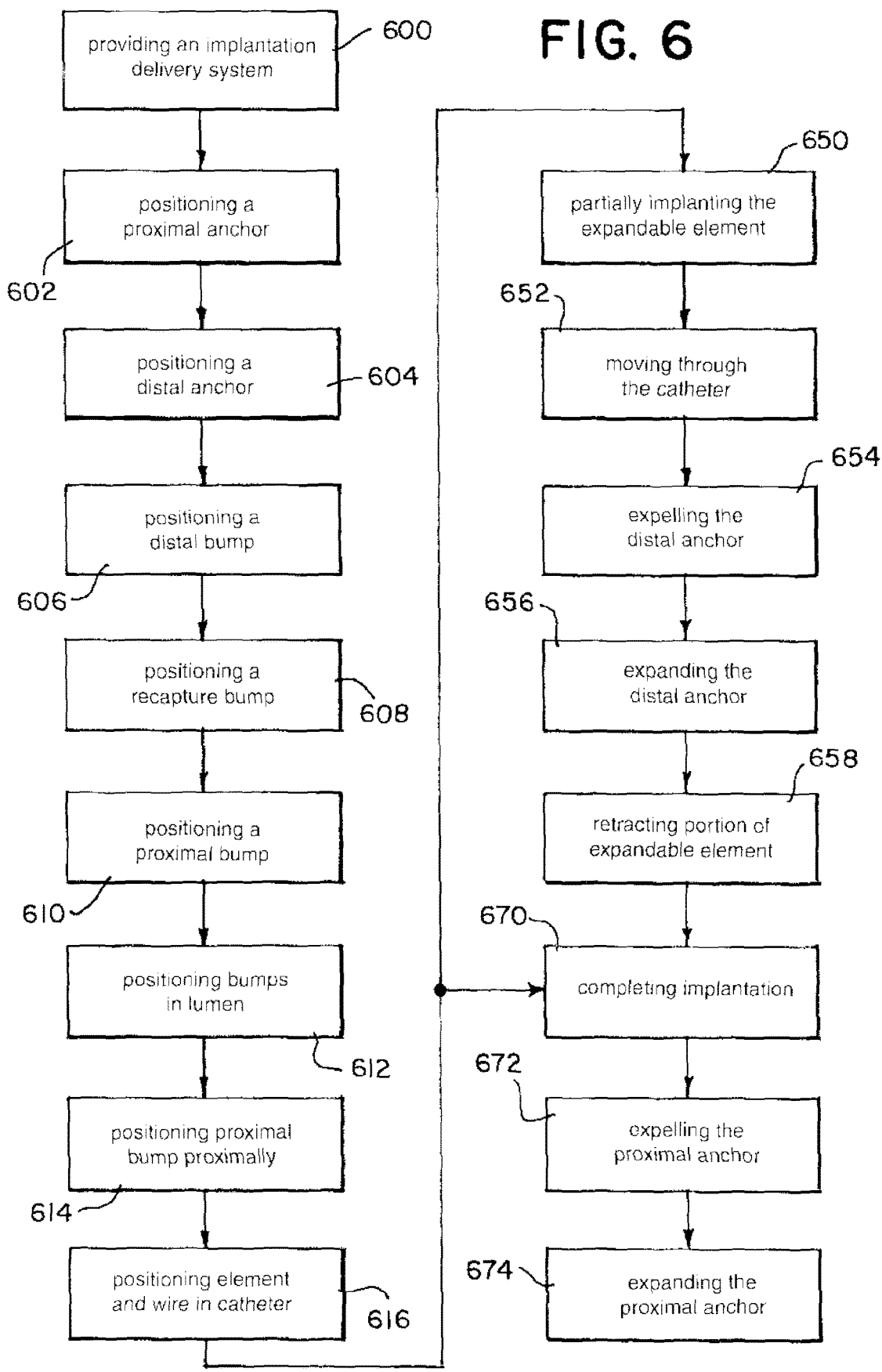

BRAID IMPLANT DELIVERY AND RETRACTION DEVICE WITH DISTAL ENGAGEMENT

CROSS REFERENCE TO RELATED APPLICATIONS

This application is a Continuation-In-Part of U.S. application Ser. No. 13/802,114 filed Mar. 13, 2013.

FIELD OF THE DISCLOSURE

This disclosure relates generally to devices for interventional therapeutic treatment or vascular surgery for treatment of defects in the vasculature, and more particularly concerns a system for delivering a self-expanding device or stent to a treatment site in a body lumen of a patient.

BACKGROUND

Cardiac stents, which are an example of a self-expanding device, are inserted into a blood vessel to provide an open path within the blood vessel, have been widely used in intravascular angioplasty treatment of occluded cardiac arteries, and in other applications. Stents are often deployed by use of inflatable balloons, or mechanical devices which force the stent open, thereby reinforcing the artery wall and provide a clear through-path in the center of the artery after the angioplasty procedure to prevent restenosis. The use of placement techniques, such as balloons or mechanical expansions of the type often found to be useful in cardiac surgery, are relatively less useful in vasoocclusive surgery, particularly when tiny vessels, such as those found in the brain, are to be treated.

Other stents are self-expanding and are just deployed inside of the vascular. Their self-expanding nature allows them to be smaller as well as the devices to deploy them. There are different techniques to deploy the stents, and each has benefits and drawbacks. One expandable stent and delivery system is known that includes an expandable stent having proximal and distal anchor members mounted on proximal and distal legs extending proximally and distally from the stent. The proximal and distal anchor members of the expandable stent are mounted in gaps formed between proximal, intermediate and distal cylindrical members disposed on and spaced apart along an elongated core member. However, pushing the device distally in a catheter from the proximal end of the device is not optimal, because application of force in a distal direction on the proximal end of the stent can axially compress the stent, and can cause the stent to expand radially. Likewise, retracting the device proximally may not be optimal either, because application of force in a proximal direction on the distal end of the stent also can axially compress the stent, and can cause the stent to expand radially.

Some known implant deployment techniques utilize members extending from a delivery wire positioned outside the stent which push against the stent proximally or distally depending on distal or proximal placement of the members in relation to the stent. See, U.S. Pat. Nos. 6,123,723, 6,280,465, and US Publication No. 2011/0307049. Other techniques deploy the members inside of the stent. See, US Publication No. 2014/0277360, and U.S. Pat. Nos. 5,702,418, and 6,955,685, all of which are incorporated herein by reference. Such techniques may result in the members of the delivery system becoming caught on a deployed implant during extraction of the delivery wire and subsequently altering the position of the implant in the anatomy. Such techniques may also require several members which can increase the likelihood of altering the position of the implant during extraction of the delivery wire. Also, the more members on the delivery wire, the more difficult it may be to manufacture. In order to build the delivery system, a manufacturer can either secure polymer/metal sleeves onto a core wire, or grind down a core wire to create members on a wire. The more members on a delivery wire, the more material must be used to add and secure members, or, the more the grind profile has to change to accommodate all of the members.

More recently, a technique employing a dual function bump member disposed on a delivery wire and positioned within an implant, and a pusher bump member disposed on the delivery wire and positioned proximal the implant can deploy and retract the implant using only the two bump members on the delivery wire. See, US Publication No. 2018/0092766, incorporated herein by reference. While this solution can address the problems of other known techniques as discussed, the technique can require pushing or pulling the delivery wire over substantial lengths during deployment and repositioning of the implant. The dual function bump member can be positioned at the distal end of the implant during deployment and moved to the proximal end of the implant for extraction. Therefore, repositioning of the implant can involve subsequent distal and proximal movements of the delivery wire that are approximately equal to the length of the implant. Particularly for longer implants, this can increase the likelihood that deployed portions of the implant may be disturbed. Additionally, a length of delivery wire approximately equal to or longer than the stent may extend between the dual function bump and the distal coil 220 so that the distal coil 220 does not interfere with the deployed implant during retraction of the implant. In some treatments, a shorter extension of the distal coil 220 may be desired.

Thus, it would be desirable to provide a delivery system for expandable stents that offers the flexibility of deploying and retracting the stent as desired with minimal travel of the delivery wire during deployment and retraction. Also desirable is a simplified manufacturing method. The solution of this disclosure solves these and other problems of the art.

SUMMARY

An example of the delivery system described provides a solution for deploying and retracting stents utilizing at least three bump members including a distal, puller bump member positioned within the stent, an intermediate, retractor bump member positioned within the stent proximal the distal bump, and a proximal, pusher bump positioned proximal the stent. This disclosure provides a solution with a minimal number of delivery wire members that can be capable of deploying and repositioning long stents with minimal travel of the delivery wire.

An example of a braid implant delivery and retraction device having a catheter, an expandable element and a delivery wire with distal, pusher, and recapture bumps. The expandable element having compressed, partially delivered, and implanted configurations. Delivering the braid can include engaging the distal bump until the braid is in the partially delivered configuration. If the user needs to recapture the braid, the recapture bump engages the braid proximally. To fully implant the braid, the distal bump is used until the braid is partially delivered and then the distal bump disengages so that the pusher bump completes implanting by proximally pushing the braid completely out of the catheter.

An example of a vascular treatment apparatus can have a catheter with an inner lumen, an expandable element and a delivery wire. The expandable element including a proximal end, a distal end, a braided portion located between the proximal end and the distal end having a lumen therebetween, a proximal anchor member disposed at the proximal end, and a distal anchor member disposed at the distal end. The expandable element can have a compressed configuration dimensioned to fit within the inner lumen of the catheter; and a partially implanted configuration wherein the proximal end is dimensioned to fit within the inner lumen of the catheter and the distal end is dimensioned larger than the catheter.

In some examples, the delivery wire can be disposed within and extending through the inner lumen and the expandable element, and can include a proximal portion, a first intermediate portion located distal the proximal portion, a second intermediate portion located distal the first intermediate portion, a distal portion located distal the second intermediate portion, a pusher bump member located adjacent the proximal portion and the first intermediate portion, a recapture bump member located adjacent the first intermediate portion and second intermediate portion, and a distal bump member located adjacent the second intermediate portion and the distal portion.

In some examples, the expandable element can be movable from the compressed configuration to the partially implanted configuration by a distal movement of the delivery wire causing the distal bump member of the delivery wire to engage with the distal anchor member of the expandable element and push the distal anchor member distally, thereby expelling the distal anchor member from the catheter, and the delivery wire is movable distally and proximally in relation to the expandable element in the partially implanted configuration.

An example of the expandable element can also be retractable from the partially implanted configuration by a proximal movement of the delivery wire causing the recapture bump member to engage with the proximal anchor member of the expandable element and push the proximal anchor member proximally, thereby retracting at least a portion of the expandable element into the catheter.

An example of the expandable element can be movable from the partially implanted configuration to an implanted configuration by a distal movement of the delivery wire causing the pusher bump member of the delivery wire to engage with the proximal anchor member of the expandable element and push the proximal anchor member distally, thereby expelling the proximal end of the expandable element from the catheter.

When the expandable element is in the compressed configuration and is positioned entirely within the inner lumen of the catheter, the distal bump member is positioned within the lumen of the braided portion of the expandable element, the recapture bump member is positioned within the lumen of the braided portion of the expandable element, and the proximal bump member is positioned proximal the proximal anchor member.

When the expandable element is in the partially implanted configuration, the distal end of the expandable element is positioned outside the catheter, the proximal end and the proximal anchor of the expandable element are positioned within the inner lumen of the catheter, and the recapture bump is movable to retract at least a portion of the expandable element into the lumen of the catheter. At least one of distal bump member, recapture bump member, and proximal bump member comprise radio-opaque material and no more than one bump member is capable of engaging an anchor member at any time.

An example of the braided portion of the expandable element can be a plain weave, self-expanding and can at least occlude a neck of an aneurysm, and/or support embolic material within the aneurysm.

An example of a method of deploying an implant has steps of providing an implantation delivery system comprising a catheter, an expandable element, and a delivery wire; positioning a proximal anchor at a proximal end of the expandable element and positioning a distal anchor at a distal end of the expandable element. Positioning a distal bump on the delivery wire, positioning a recapture bump on the delivery wire proximal to the distal bump, positioning a proximal bump on the delivery wire proximal to the recapture bump, positioning the distal bump and the recapture bump within a lumen of the expandable element, positioning the proximal bump proximal to the expandable element, and positioning the expandable element and at least a portion of the delivery wire within a lumen of the catheter.

The method can also include partially implanting the expandable element, having steps of moving the distal anchor and the expandable element distally through the lumen of the catheter by pushing the delivery wire distally thereby pushing the distal bump against the distal anchor while the proximal bump and recapture bump remain disengaged from the expandable element, expelling the distal anchor from a distal end of the catheter by pushing the delivery wire distally thereby pushing the distal bump against the distal anchor while the proximal bump and recapture bump remain disengaged from the expandable element and expanding the expelled distal anchor, thereby disengaging the distal bump from the expandable element. In some examples, the method can include retracting at least a portion of the expandable element into the catheter can be accomplished by pulling the delivery wire proximally thereby pulling the recapture bump against the proximal anchor while the distal bump and the proximal bump remain disengaged from the expandable element.

In some examples, the method can include completing implantation of the expandable element, can have the steps of expelling the proximal anchor from the distal end of the catheter by pushing the delivery wire distally thereby disengaging the recapture bump from the expandable element and pushing the proximal bump against the proximal anchor; and expanding the expelled proximal anchor, thereby disengaging the proximal bump.

Another example of the method can have steps of moving the delivery wire independently from the expandable element while maintaining the proximal anchor within the lumen of the catheter and positioning the expandable element within a bodily lumen. The method can include the steps of positioning the expandable element to occlude the neck of an aneurysm and positioning the expandable element to support embolic material in the aneurysm.

An example of a stent implantation system can have a catheter; a braided stent can have a first expandable anchor at a distal end and a second expandable anchor at a proximal end, and the braided stent is movable in a compressed configuration through the catheter. Also, the braided stent is movable to a partially implanted configuration such that first expandable anchor is expanded in an implanted position distal to the catheter and the second expandable anchor is compressed within the catheter.

Another example of a delivery wire comprising a pusher bump, a puller bump, and a recapture bump, the delivery wire extends through the braided stent when the braided stent is in the compressed configuration and when the braided stent is in the partially implanted configuration. The pusher bump is positioned proximal the second expandable anchor when the braided stent is in the compressed configuration and when the braided stent is in the partially implanted configuration. The puller bump and the recapture bump are positioned within the braided stent when the braided stent is in the compressed configuration, A distal movement of the delivery wire when the braided stent is in the compressed configuration pushes the puller bump against the first expandable anchor to move the expandable element distally while the pusher bump and recapture bump are disengaged from the expandable element. A distal movement of the delivery wire when the braided stent is in the partially implanted configuration pushes the pusher bump against the second expandable anchor to move the expandable element distally while the puller bump and recapture bump are disengaged from the expandable element. A proximal movement of the delivery wire when the braided stent is in the partially implanted configuration pulls the recapture bump against the second expandable anchor to move the expandable element proximally while the puller bump and pusher bump are disengaged from the expandable element.

An example of the system can have the first expandable anchor is sized larger than a diameter of puller bump when the braided stent is in the partially implanted configuration. Further, the first expandable anchor can be sized to remain anchored independent of any movement of the puller bump when the braided stent is in the partially implanted configuration. Also, the first expandable anchor is freed from the puller bump when the braided stent is in the partially implanted configuration.

BRIEF DESCRIPTION OF THE DRAWINGS

This disclosure is described with particularity in the appended claims. The above and further aspects of this disclosure may be better understood by referring to the following description in conjunction with the accompanying drawings, in which like numerals indicate like structural elements and features in various Figures. The drawings are not necessarily to scale, emphasis instead being placed upon illustrating the principles of the disclosure. The drawings depict one or more implementations in accord with the present teachings, by way of example only, not by way of limitation.

FIGS. 3A and 3B illustrate extension and compression of an implant mesh within the catheter;

FIG. 4 illustrates a braided implant according to an example of the disclosure; and FIGS. 5A to 5H illustrate example steps for a method of use of an implantation system according to an example of the disclosure.

FIG. 6 illustrates example steps for a method of use of an implantation system according to an example of the disclosure.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
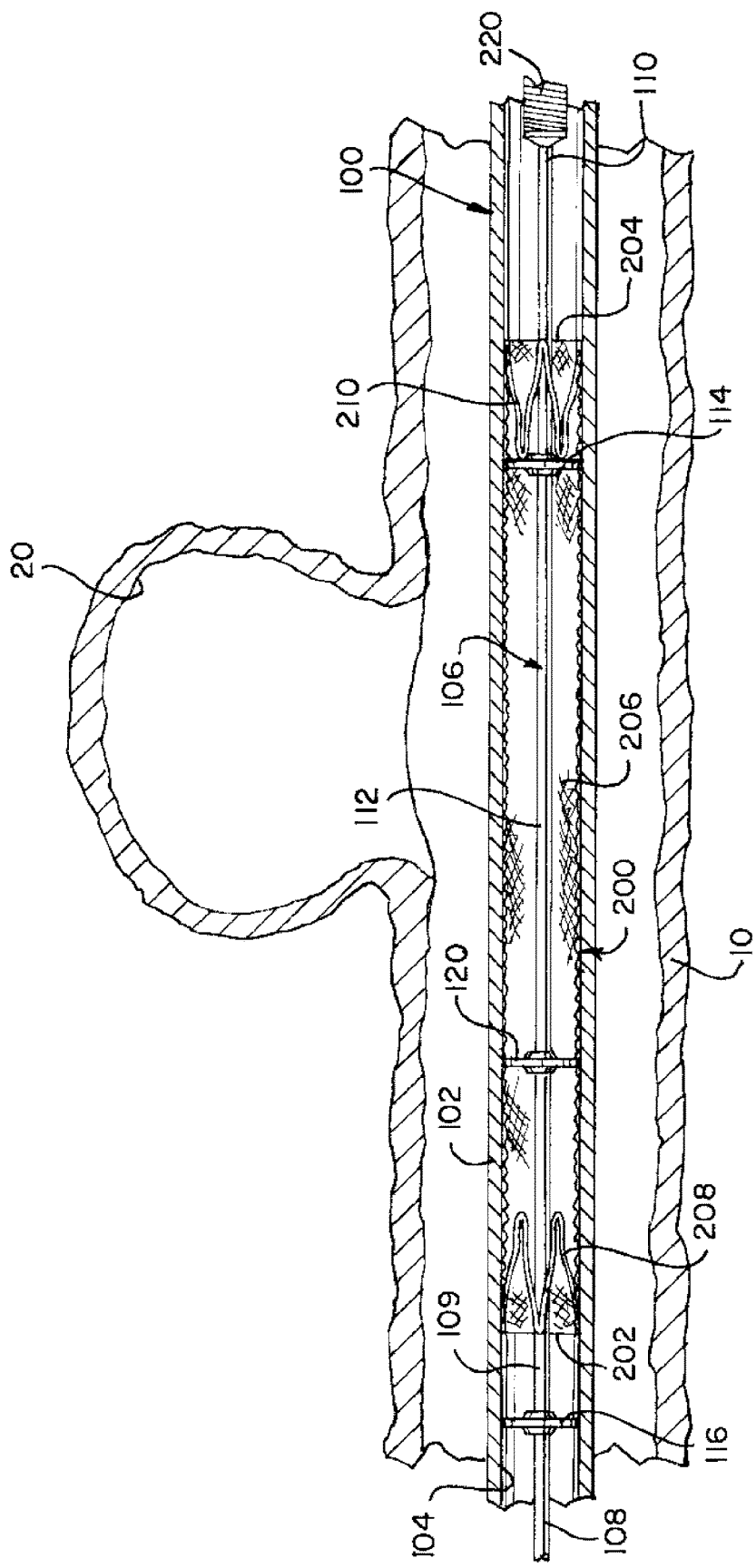
FIG. 1 illustrates a cut-away view of an apparatus for delivering and releasing a expandable element to a treatment site in a patient's body lumen, according to an example of the disclosure.

Examples of the present disclosure provides for a vascular treatment apparatus 100 that can deliver and release an expandable element 200 to a treatment site, including an aneurysm 20 in a patient's body lumen (e.g. vasculature) 10. As is illustrated in FIG. 1, the apparatus 100 can include a catheter 102 comprising an inner lumen 104. The expandable element 200 has a proximal end 202, a distal end 204, a braided portion 206 located between the proximal end 202 and the distal end 204, and also forms a lumen therebetween. The expandable element 200 also includes a proximal anchor member 208 disposed at the proximal end 202, and a distal anchor member 210 disposed at the distal end 204. In certain examples, the proximal and distal anchors 208,210 face away from each other, the proximal anchor 208 facing the proximal end 202, and the distal anchor 210 facing the distal end 204. See, FIG. 4.

The one or more anchor members 208, 210, can be projections which extend generally parallel to a longitudinal axis of the expandable element 200 and extend downward toward the longitudinal axis of the expandable element 200. The anchor members 208, 210 can serves as a radiopaque marker for improved visualization during the deployment of the expandable element 200 within the body lumen 10. The anchor members 208, 210 can be used to align the expandable element 200 so it can be pushed and pulled through the catheter 102 without damage or deformation. The anchor members 208, 210 can also be used to move the braided portion 206 into an expanded/implanted configuration. An example of the anchor member 208, 210 can be found in U.S. Ser. No. 15/299,918, the entirety of which is incorporated herein by reference.

Typically, the expandable element 200 can have a compressed configuration and an expanded, implanted, configuration. In the compressed configuration the expandable element 200 can be dimensioned to fit within the inner lumen 104 of the catheter 102. In certain examples, the catheter 102 can aid in constraining the expandable element 200 so it does not expand when contained within the catheter 102. Other elements can be used to constrain the expandable element 200 as are known in the art.

The expandable element 200 can also have a partially implanted configuration where the proximal end 202 is dimensioned to fit within the inner lumen 104 of the catheter 102 and the distal end 204 is dimensioned larger than the catheter 102. See, e.g., FIG. 5C.

Another element of the apparatus 100 is a delivery wire 106 disposed within and extending through the inner lumen 104 of both the catheter 102 and the expandable element 200. An example of the delivery wire 106 can have a proximal portion 108, a first intermediate portion 109 located distal the proximal portion 108, a second intermediate portion 112 located distal of the first intermediate portion 109, and a distal portion 110 located distal of the second intermediate portion 112.

The delivery wire 106 can have a distal bump member 114, a recapture bump member 120, and a pusher bump member 116 extending radially outwardly from the delivery wire 106 and configured to engage the anchor members 208, 210 when the delivery wire 106 is translated longitudinally toward the anchor members 208, 210. One or all of the bump members 114, 116, 120 can be a radiopaque material to allow the location of the bumps 144, 116, 120 to be readily visible during an implanting procedure. The bumps 114, 116, 120 can be formed as larger diameter surfaces of the distal wire 106. They can be formed separately and added to the wire 106 or formed as the wire 106 is formed by selective addition or removal or material as the wire 106 is ground or laser cut. The bumps 114, 116, 120 can be any shape, as long as they can easily engage and disengage the expandable element 200.

The pusher bump member 116 can be located adjacent the proximal portion 108 and the first intermediate portion 109. The recapture bump member 120 can be located adjacent the first intermediate portion 109 and second intermediate portion 112. The distal bump member 114 can be located adjacent the second intermediate portion 112 and the distal portion 110. Force applied longitudinally to the delivery wire 106 can be transmitted through any of the bump members 114, 116 to the anchor members 208, 210 of the expandable element 200. This transfer of force can displace the expandable element 200 through the catheter 102 and the body lumen 10. In one example, no more than one bump member 114, 116, 120 is capable of engaging an anchor member 208, 210 at any time.

Figure 5A:
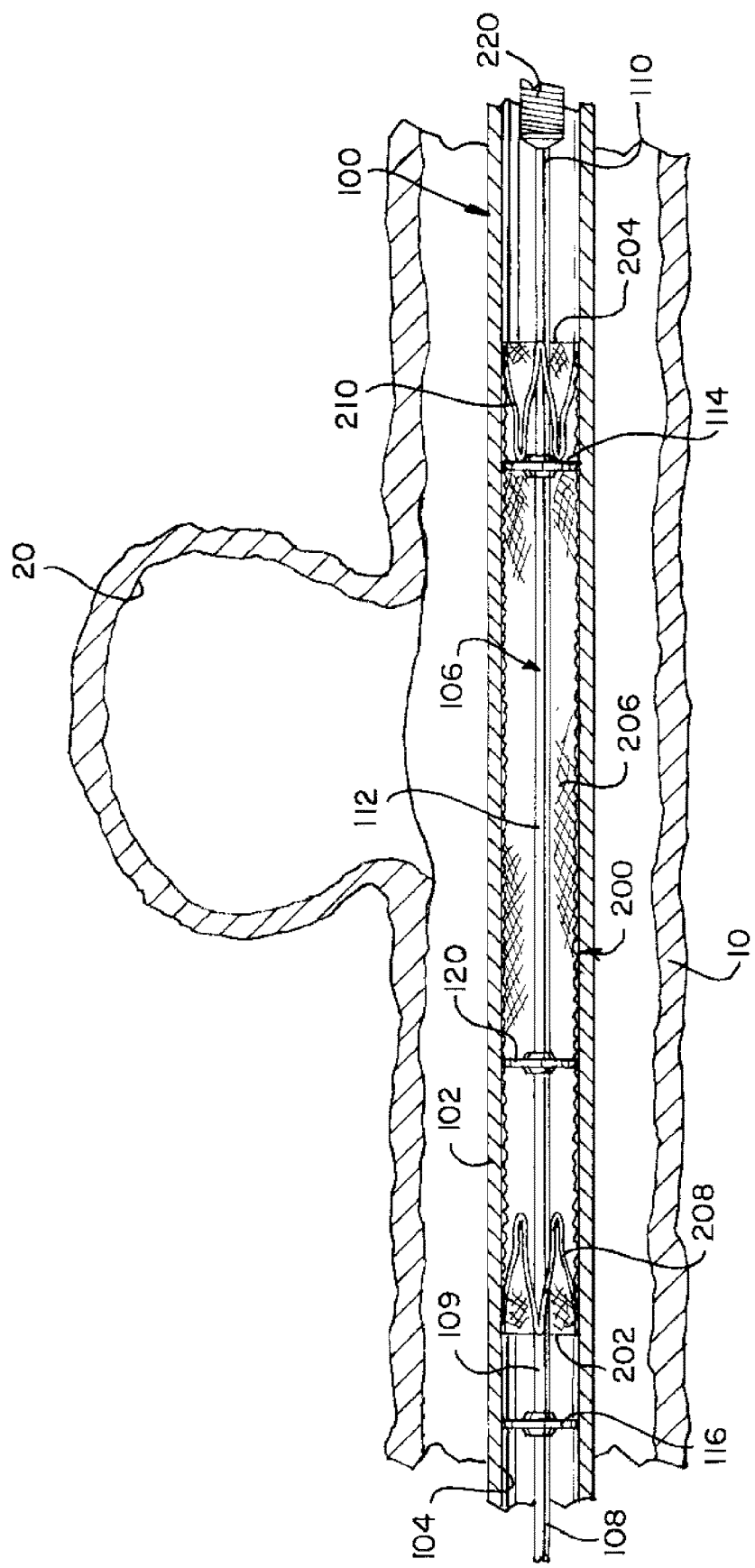
Figure 5B:
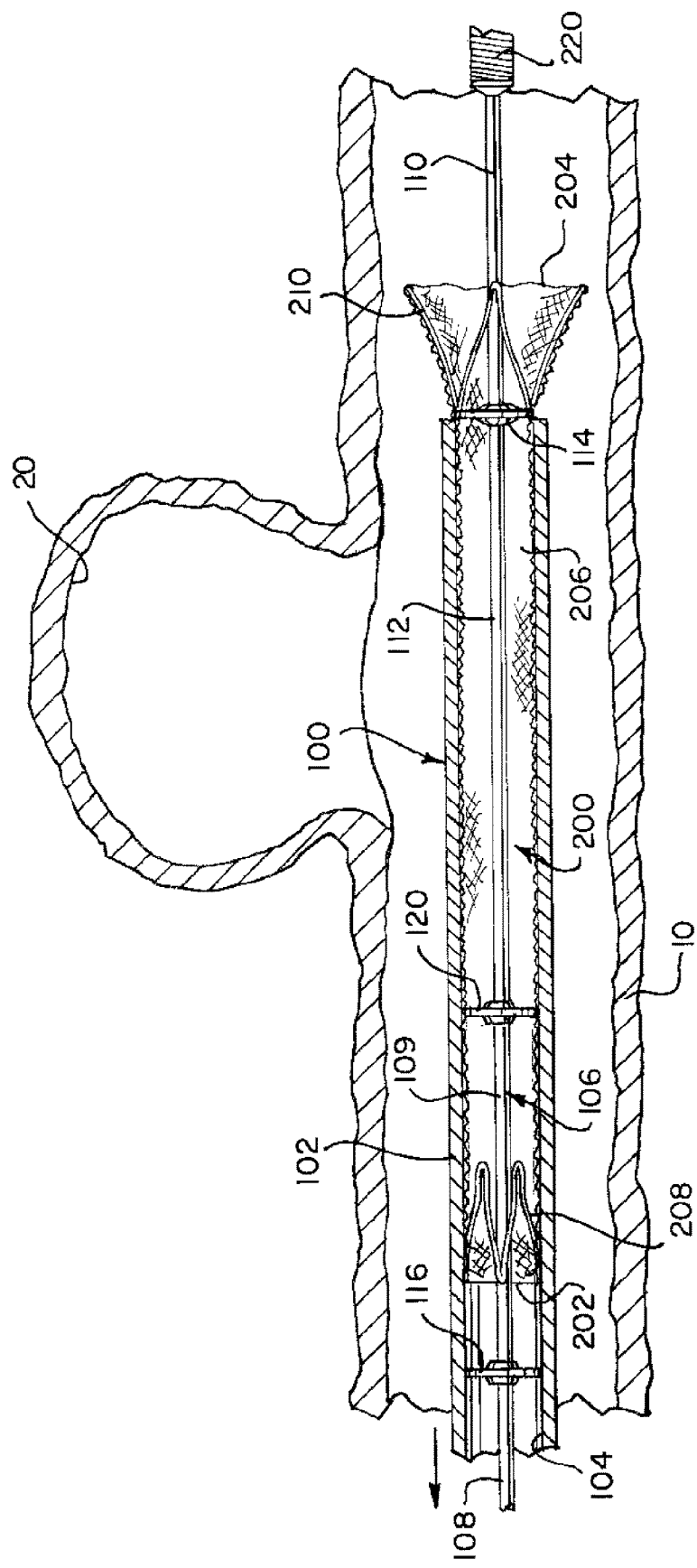
Figure 5C:
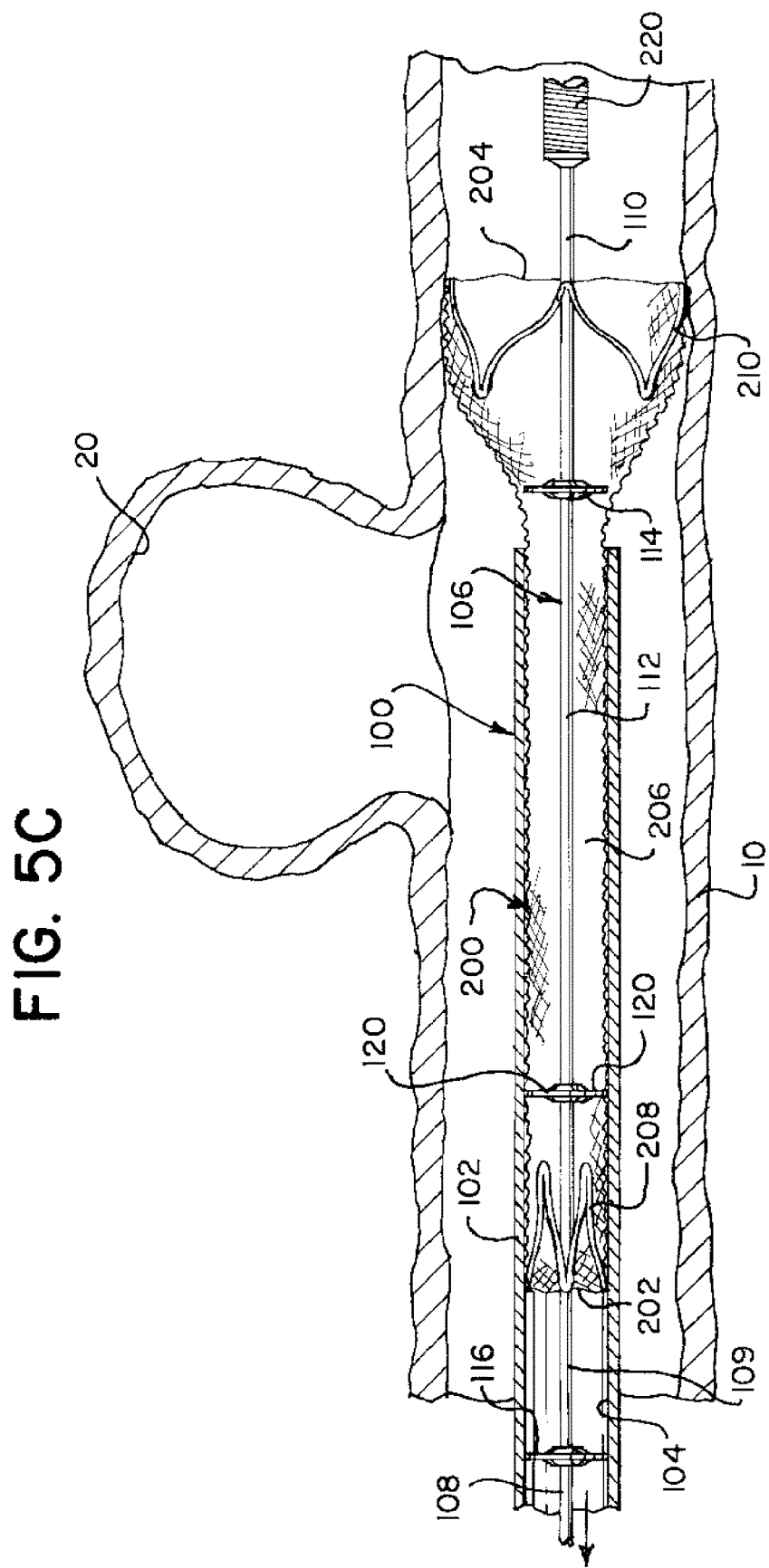
Figure 5E:
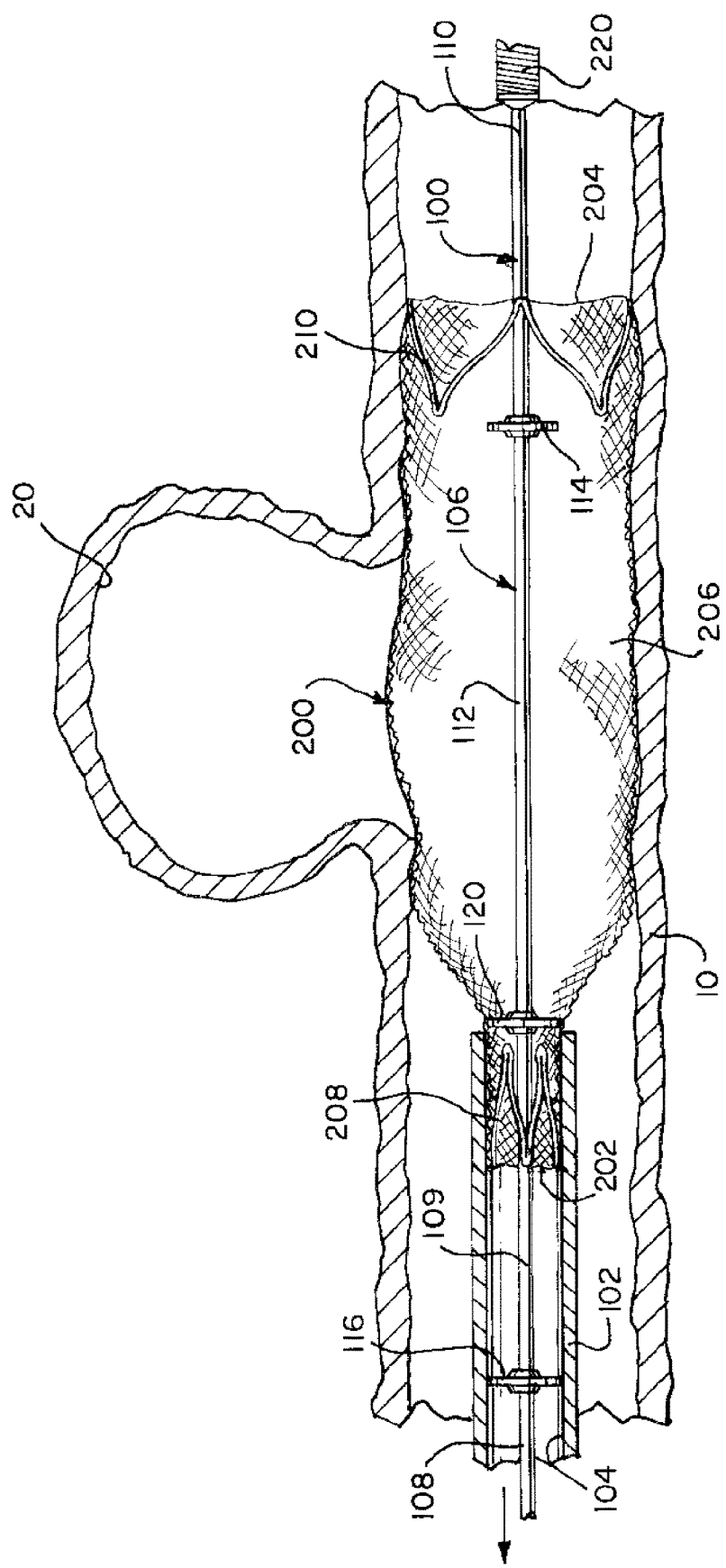

As noted above, the expandable element 200 can be moved from a compressed configuration illustrated in FIG. 1 to a partially implanted configuration illustrated in FIG. 5C. Distal movement of the delivery wire 106 can cause the distal bump member 114 of the delivery wire 106 to engage with the distal anchor member 210 of the expandable element 200 and push the distal anchor member 210 distally, thereby expelling the distal anchor member 210 from the catheter 102. The delivery wire 106 can be further capable of moving distally and proximally in relation to the expandable element 200 in the partially implanted configuration, as illustrated in FIG. 5C.

Figure 5F:
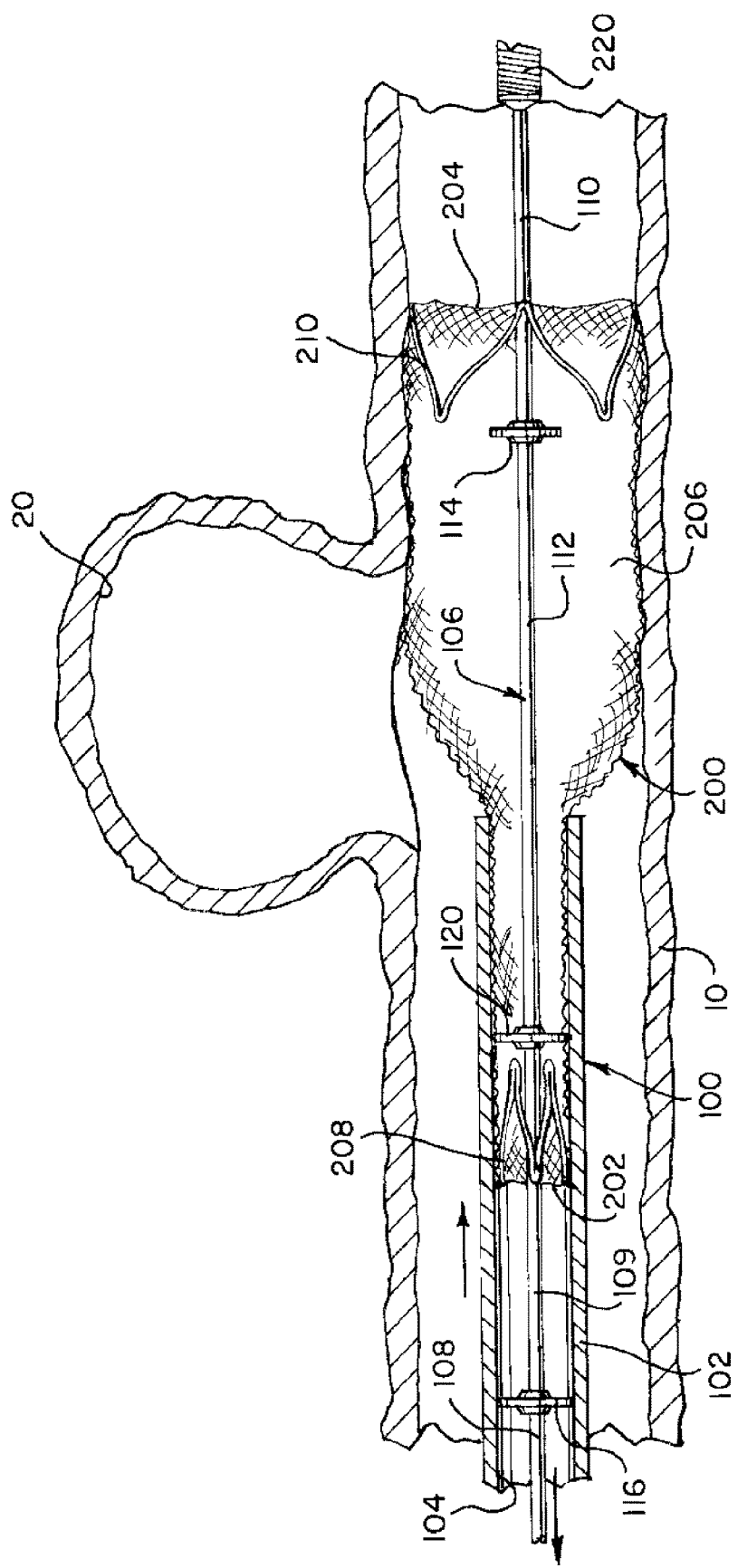

During a procedure, if the user is dissatisfied with the placement of the expandable element 200, the expandable element 200 can be retracted back into the catheter 102 so it can be repositioned. FIG. 5F illustrates a recapture of the expandable element 200 from the partially implanted configuration using a proximal movement of the delivery wire 106 causing the recapture bump member 120 to engage with the proximal anchor member 208 of the expandable element 200 and push the proximal anchor member 208 proximally, thereby retracting at least a portion of the expandable element 200 into the catheter 102.

Figure 5G:
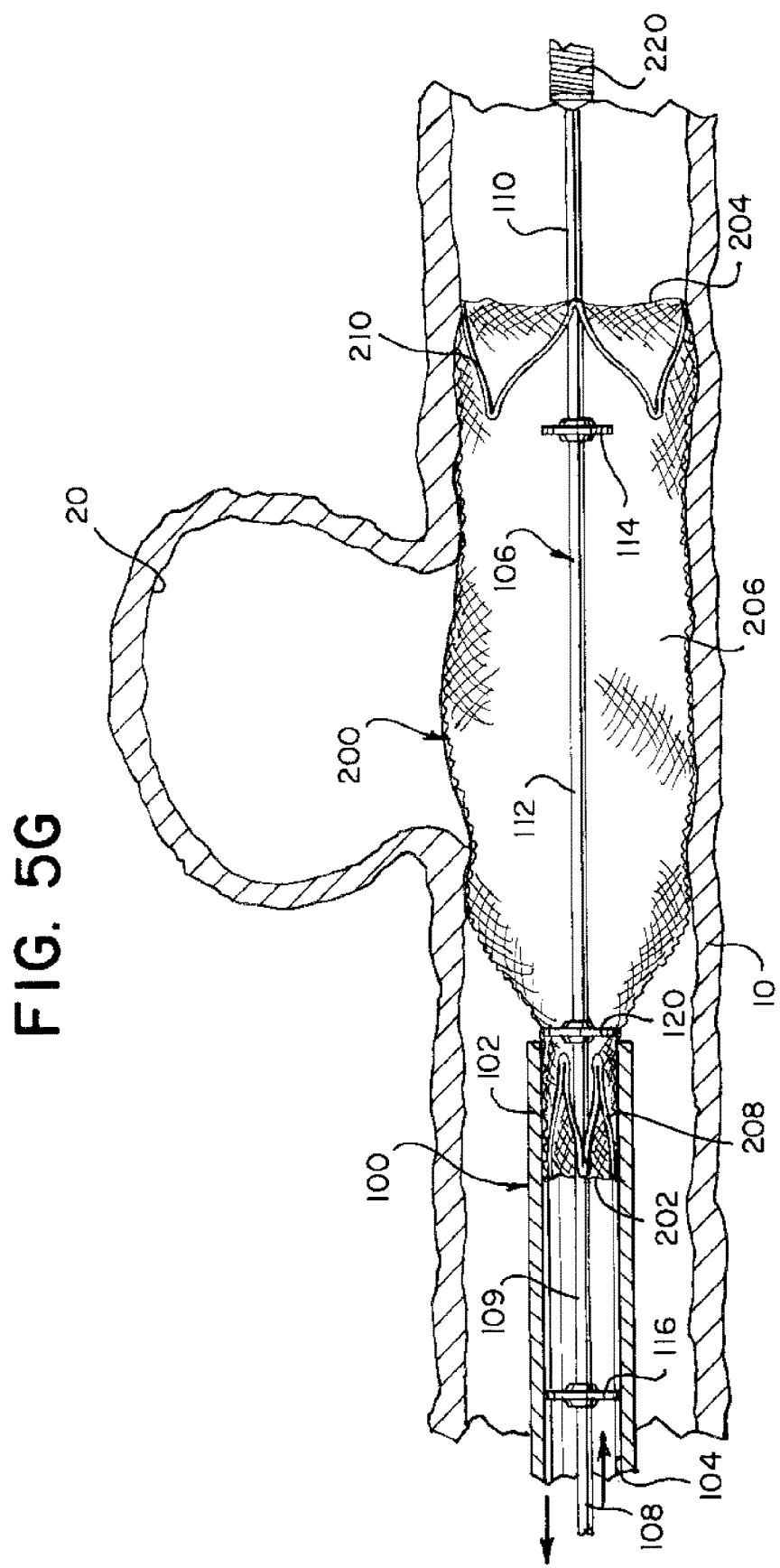

In an example, during a procedure, once the user is satisfied with the expandable element's 200 placement, the expandable element 200 can be moved from the partially implanted configuration illustrated in FIG. 5G to an implanted configuration illustrated in FIG. 5H. Implanting the expandable element 200 can be done by a distal movement of the delivery wire 106 causing the pusher bump member 116 of the delivery wire 106 to engage with the proximal anchor member 208 of the expandable element 200 and push the proximal anchor member 208 distally. This expels the proximal end 202 of the expandable element 200 from the catheter 102.

In the expanded configuration, as illustrated in FIG. 5H, the expandable element 200 expands radially to fit the vessel diameter of the patient's body lumen 10. The expanded dimension of the expandable element 200 allows the apparatus 100 to pass therethrough, to either advance to a second location or be withdrawn. The expandable element 200 can be expandable under its inherent proprieties, based at least on its original shape and the nature of the materials that make up the element. Examples of the expandable element 200 can be one of pear shaped, ovoid, elliptical and the like when at its expanded diameter. The construction of the expandable element 200 is known to those of skill in the art. Other embodiments are contemplated for expandable elements 200 of this disclosure and can also be observed in U.S. Pat. Pub. 2016/0058524, a reference that is incorporated in its entirety herein.

Figure 2A:
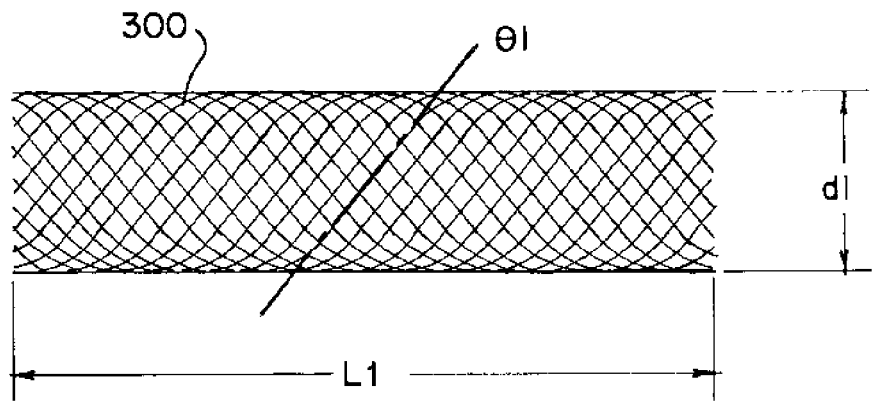
FIGS. 2A to 2C illustrate extension and compression of an implant mesh.
Figure 2B:
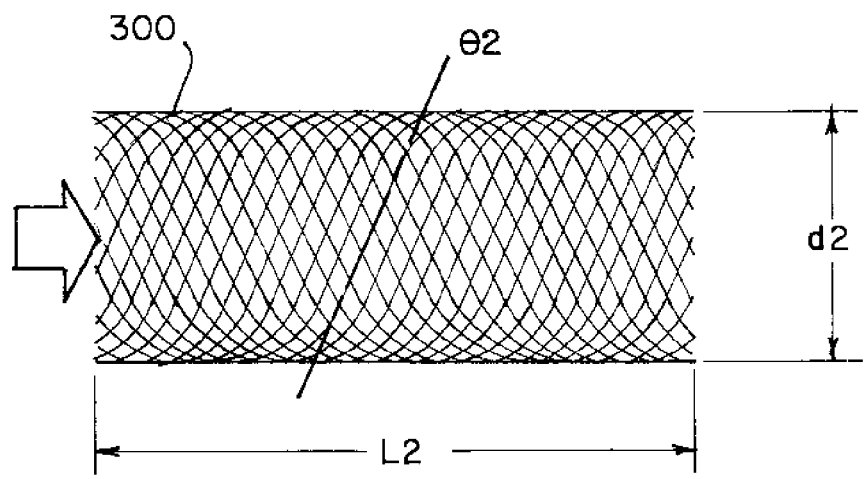
Figure 2C:
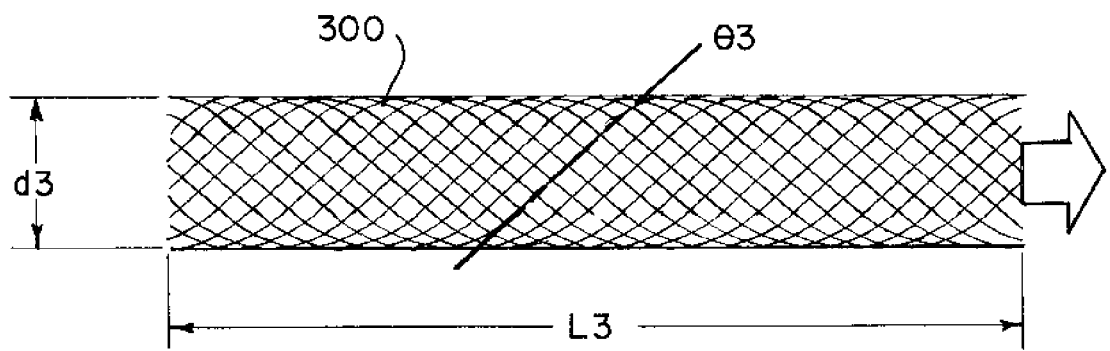

FIGS. 2A to 2C illustrate an example of a braided mesh that could be used to make an expandable element 200. If FIG. 2A, the braid 300 is shown without any forces applied and it has a length L1, a diameter d1 and the pores of the mesh have a particular angle θ1. Stationary angle θ1 of the mesh is a feature that can determine the porosity of the braid 300 at that configuration. FIG. 2B illustrates when a proximal "pushing" force is applied to the braid 300, whereby the "pushing" force is demonstrated with a proximal arrow applied to the braided mesh. With this force applied, the braid 300 has a tendency to "bunch" causing its diameter d2 to increase, while it "pushed" length L2 is decreased. This also can increase the pore angle θ2. Thus, under "pushing" conditions, L1>L2, d1<d2, and θ1<θ2. FIG. 2C illustrates when a "pull" force is applied to a distal end of the braid 300, whereby the "pulling" force is demonstrated with a distal arrow applied away from the braided mesh. Here, the braid 300 extends (L3) and its diameter d3 shrinks in relation to the rest condition. The pore angle θ3 is smaller, again changing the porosity of the braid 300. The relationships are now that L1<L3, d1>d3, and θ1>θ3. In relation to each other L2<L1<L3; d3<d1<d2; θ3<θ1<θ2.

The above features of a braid 300 can then lead to difficulties in delivering it as the expandable member 200 through the catheter lumen 104. FIG. 3A illustrates that as the braid 300 is pushed through the catheter 102, the expansion in diameter (d2) can cause the braid 200 and the walls of the catheter lumen 104 to come into contact. This can increase the force needed to move the braid 300 through the catheter 102 to the aneurysm 20 and may damage the braid 300 during delivery. One solution can be to increase the diameter of the catheter to be greater than the "pushed" diameter d2, however this then limits the access of the catheter and braid to distal portions of the neurovascular. In these types of procedures, the smaller the diameter is more preferable.

A pulling force, however, as illustrated in FIG. 3B can cause the braid 300 to be reduced to its "pulled" diameter d3 which can be smaller than the diameter of the catheter lumen 104. This allows the braid 300 to travel through the catheter 102 with less friction and a reduced chance of damage to the braid 300 during delivery.

The braid 300/braided portion 206 of the expandable element 200 can be a plain weave and can be a self-expanding element. As illustrated in FIG. 5H the braided portion 206 can occludes a neck of an aneurysm 20 and further, can support embolic material (not illustrated) within the aneurysm 20.

In certain examples, when expandable element 200 is in the compressed configuration it can be positioned entirely within the inner lumen 104 of the catheter 102. Then, the distal bump member 114 can be positioned within the lumen of the braided portion 206 of the expandable element 200, the recapture bump member 120 can be positioned within the lumen of the braided portion 206 of the expandable element 200, and the proximal bump member 116 can be positioned proximal the proximal anchor member 208. See, FIG. 1

In certain examples where the expandable element 200 is in the partially implanted configuration, the distal end 204 of the expandable element 200 can be positioned outside the catheter 102, the proximal end 202 and the proximal anchor 208 of the expandable element 200 are positioned within the inner lumen 104 of the catheter 102, and the recapture bump 120 is movable to retract at least a portion of the expandable element 200 into the lumen 104 of the catheter 102.

As FIG. 4 illustrates, when the expandable element 200 is in the (fully) implanted configuration, both anchors 208, 210 and the braided portion 206 are in their expanded position. Once implanted, the expandable element 200 can divert blood flow from the aneurysm 20, allowing it to gradually shrink. Diversion and/or shrinkage can reduce the chance of rupture, and thus, hemorrhagic stroke.

FIGS. 5A-5H and 6 illustrate an example of a method of deploying an implant. The steps can include providing an implantation delivery system 100 comprising a catheter 102, an expandable element 200, and a delivery wire 106 (Step 600), positioning a proximal anchor 208 at a proximal end 202 of the expandable element 200 (Step 602), and positioning a distal anchor 210 at a distal end 204 of the expandable element 200 (Step 604). A distal bump 114 can be positioned on the delivery wire 106 (Step 606), a recapture bump 120 can be positioned on the delivery wire 106 proximal to the distal bump 114 (Step 608); and a proximal bump 116 can be positioned on the delivery wire 106 proximal to the recapture bump 120 (Step 610). Positioning the distal bump 114 and the recapture bump 120 within a lumen of the expandable element 200 (Step 612), positioning the proximal bump 116 proximal to the expandable element 200 (Step 614), and positioning the expandable element 200 and at least a portion of the delivery wire 106 within a lumen 104 of the catheter 102 (Step 616).

Further steps include partially implanting the expandable element 200 (Step 650), which can have the steps of moving the distal anchor 210 and the expandable element 200 distally through the lumen 104 of the catheter 102 by pushing the delivery wire 106 distally thereby pushing the distal bump 114 against the distal anchor 210 while the proximal bump 116 and recapture bump 120 remain disengaged from the expandable element 200 (Step 652). Expelling the distal anchor 210 from a distal end of the catheter 102 by pushing the delivery wire 106 distally thereby pushing the distal bump 114 against the distal anchor 210 while the proximal bump 116 and recapture bump 120 remain disengaged from the expandable element 200 (Step 654) and expanding the expelled distal anchor 210, thereby disengaging the distal bump 114 from the expandable element 200 (Step 656).

In certain examples, the method can include the step of retracting at least a portion of the expandable element 200 into the catheter 102 by pulling the delivery wire 106 proximally thereby pulling the recapture bump 120 against the proximal anchor 208 while the distal bump 114 and the proximal bump 116 remain disengaged from the expandable element 200 (Step 658).

Completing implantation of the expandable element 200 (Step 670) can include expelling the proximal anchor 208 from the distal end of the catheter 102 by pushing the delivery wire 106 distally thereby disengaging the recapture bump 120 from the expandable element 200 and pushing the proximal bump 116 against the proximal anchor 208 (Step 672) and expanding the expelled proximal anchor 208, thereby disengaging the proximal bump 116 (Step 674).

Steps of other examples can include moving the delivery wire 106 independently from the expandable element 200 while maintaining the proximal anchor 208 within the lumen 104 of the catheter 102, positioning the expandable element 200 within a bodily lumen 10 to then occlude the neck of an aneurysm 20. Further including positioning the expandable element 200 to support embolic material in the aneurysm 20.

Another example of the present disclosures can be considered a stent implantation system having a catheter 102, a braided stent 200 with a first expandable anchor 210 at a distal end 204 and a second expandable anchor 208 at a proximal end 202. The braided stent 200 can be movable in a compressed configuration through the catheter 102 and can be movable to a partially implanted configuration such that first expandable anchor 210 is expanded in an implanted position distal to the catheter 102 and the second expandable anchor 208 is compressed within the catheter 102. A delivery wire 106 can include a pusher bump 116, a puller bump 114, and a recapture bump 120, and the delivery wire 106 extends through the braided stent 200 when the braided stent is in the compressed configuration and when the braided stent 200 is in the partially implanted configuration. The pusher bump 116 can be positioned proximal the second expandable anchor 208 when the braided stent 200 is in the compressed configuration and when the braided stent 200 is in the partially implanted configuration, and the puller bump 114 and the recapture bump 120 can be positioned within the braided stent 200 when the braided stent 200 is in the compressed configuration, A distal movement of the delivery wire 106 when the braided stent 200 is in the compressed configuration pushes the puller bump 114 against the first expandable anchor 210 to move the expandable element 200 distally while the pusher bump 116 and recapture bump 120 are disengaged from the expandable element 200. The distal movement of the delivery wire 106 when the braided stent 200 is in the partially implanted configuration pushes the pusher bump 116 against the second expandable anchor 208 to move the expandable element 200 distally while the puller bump 114 and recapture bump 120 are disengaged from the expandable element 200. Also, a proximal movement of the delivery wire 106 when the braided stent 200 is in the partially implanted configuration pulls the recapture bump 120 against the second expandable anchor 208 to move the expandable element 200 proximally while the puller bump 114 and pusher bump 116 are disengaged from the expandable element.

In other examples, the first expandable anchor 210 can be sized larger than a diameter of puller bump 114 when the braided stent 200 is in the partially implanted configuration. Also, the first expandable anchor 210 can be sized to remain anchored independent of any movement of the puller bump 114 when the braided stent 200 is in the partially implanted configuration and the first expandable anchor 210 can be freed from the puller bump 114 when the braided stent 200 is in the partially implanted configuration.

Note that certain features of the apparatus 100 can be formed from materials that have a shape memory structure. For example, a metal alloy such as nickel titanium (NiTi), also known as Nitinol. Other elements may be formed of a non-superelastic material, such as spring steel or MP35N, an alloy of 35% nickel, 35% cobalt, 20% chromium, and 10% molybdenum, by weight. Features may be laser cut from the material, secure onto the delivery wire, or the delivery wire can be grinded down to create the above described elements.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A vascular treatment apparatus, comprising:
a catheter comprising an inner lumen;
an expandable element comprising:
　a proximal end;
　a distal end;
　a braided portion located between the proximal end and the distal end comprising a lumen therebetween;
　a proximal anchor member disposed at the proximal end;
　a distal anchor member disposed at the distal end;
　wherein the expandable element comprises a compressed configuration dimensioned to fit within the inner lumen of the catheter; and
　wherein the expandable element comprises a partially implanted configuration wherein the proximal end is dimensioned to fit within the inner lumen of the catheter and the distal end is dimensioned larger than the catheter; and
a delivery wire disposed within and extending through the inner lumen and the expandable element, comprising:
　a proximal portion;
　a first intermediate portion located distal the proximal portion;
　a second intermediate portion located distal the first intermediate portion;
　a distal portion located distal the second intermediate portion;
　a pusher bump member located adjacent the proximal portion and the first intermediate portion;
　a recapture bump member located adjacent the first intermediate portion and second intermediate portion; and
　a distal bump member located adjacent the second intermediate portion and the distal portion,
wherein the expandable element is movable from the compressed configuration to the partially implanted configuration by a distal movement of the delivery wire causing the distal bump member of the delivery wire to engage with the distal anchor member of the expandable element and push the distal anchor member distally, thereby expelling the distal anchor member from the catheter,
wherein the delivery wire is movable distally and proximally in relation to the expandable element in the partially implanted configuration, and
wherein the expandable element is retractable from the partially implanted configuration by a proximal movement of the delivery wire causing the recapture bump member to engage with the proximal anchor member of the expandable element and push the proximal anchor member proximally, thereby retracting at least a portion of the expandable element into the catheter.

2. The apparatus of claim 1 wherein the expandable element is movable from the partially implanted configuration to an implanted configuration by a distal movement of the delivery wire causing the pusher bump member of the delivery wire to engage with the proximal anchor member of the expandable element and push the proximal anchor member distally, thereby expelling the proximal end of the expandable element from the catheter.

3. The apparatus of claim 1 wherein,
the expandable element is in the compressed configuration and is positioned entirely within the inner lumen of the catheter,
the distal bump member is positioned within the lumen of the braided portion of the expandable element,
the recapture bump member is positioned within the lumen of the braided portion of the expandable element, and
the proximal bump member is positioned proximal the proximal anchor member.

4. The apparatus of claim 1 wherein,
the expandable element is in the partially implanted configuration,
the distal end of the expandable element is positioned outside the catheter,
the proximal end and the proximal anchor member of the expandable element are positioned within the inner lumen of the catheter, and
the recapture bump is movable to retract at least a portion of the expandable element into the lumen of the catheter.

5. The apparatus of claim 1 wherein at least one of the distal bump member, recapture bump member, and proximal bump member comprise radio-opaque material.

6. The apparatus of claim 1 wherein the braided portion of the expandable element is a plain weave.

7. The apparatus of claim 1 wherein the braid portion of the expandable element is a self-expanding element.

8. The apparatus of claim 1 wherein the braided portion is configured to occlude a neck of an aneurysm.

9. The apparatus of claim 1 wherein the braided portion is configured to support embolic material within the aneurysm.

10. The apparatus of claim 1 wherein only one bump member is capable of engaging an anchor member at any time.

11. A method of deploying an implant comprising the steps of:
providing an implantation delivery system comprising a catheter, an expandable element, and a delivery wire;
positioning a proximal anchor at a proximal end of the expandable element;
positioning a distal anchor at a distal end of the expandable element;
positioning a distal bump on the delivery wire;
positioning a recapture bump on the delivery wire proximal to the distal bump;
positioning a proximal bump on the delivery wire proximal to the recapture bump;
positioning the distal bump and the recapture bump within a lumen of the expandable element;
positioning the proximal bump proximal to the expandable element;
positioning the expandable element and at least a portion of the delivery wire within a lumen of the catheter;
partially implanting the expandable element, comprising the steps of:
　moving the distal anchor and the expandable element distally through the lumen of the catheter by pushing the delivery wire distally thereby pushing the distal bump against the distal anchor while the proximal bump and recapture bump remain disengaged from the expandable element;

expelling the distal anchor from a distal end of the catheter by pushing the delivery wire distally thereby pushing the distal bump against the distal anchor while the proximal bump and recapture bump remain disengaged from the expandable element; and expanding the expelled distal anchor, thereby disengaging the distal bump from the expandable element;

retracting at least a portion of the expandable element into the catheter by pulling the delivery wire proximally thereby pulling the recapture bump against the proximal anchor while the distal bump and the proximal bump remain disengaged from the expandable element; and completing implantation of the expandable element, comprising the steps of:

expelling the proximal anchor from the distal end of the catheter by pushing the delivery wire distally thereby disengaging the recapture bump from the expandable element and pushing the proximal bump against the proximal anchor; and expanding the expelled proximal anchor, thereby disengaging the proximal bump.

12. The method of claim 11 further comprising the step of moving the delivery wire independently from the expandable element while maintaining the proximal anchor within the lumen of the catheter.

13. The method of claim 11 further comprising the step of positioning the expandable element within a bodily lumen.

14. The method of claim 11 further comprising the step of positioning the expandable element to occlude the neck of an aneurysm.

15. The method of claim 14 further comprising the step of positioning the expandable element to support embolic material in the aneurysm.

16. A stent implantation system comprising:

a catheter;

a braided stent comprising a first expandable anchor at a distal end and a second expandable anchor at a proximal end, wherein the braided stent is movable in a compressed configuration through the catheter, and wherein the braided stent is movable to a partially implanted configuration such that first expandable anchor is expanded in an implanted position distal to the catheter and the second expandable anchor is compressed within the catheter; and a delivery wire comprising a pusher bump, a puller bump, and a recapture bump, wherein the delivery wire extends through the braided stent when the braided stent is in the compressed configuration and when the braided stent is in the partially implanted configuration, wherein the pusher bump is positioned proximal the second expandable anchor when the braided stent is in the compressed configuration and when the braided stent is in the partially implanted configuration, wherein the puller bump and the recapture bump are positioned within the braided stent when the braided stent is in the compressed configuration, wherein a distal movement of the delivery wire when the braided stent is in the compressed configuration pushes the puller bump against the first expandable anchor to move the braided stent distally while the pusher bump and recapture bump are disengaged from the braided stent, wherein a distal movement of the delivery wire when the braided stent is in the partially implanted configuration pushes the pusher bump against the second expandable anchor to move the braided stent distally while the puller bump and recapture bump are disengaged from the braided stent, and wherein a proximal movement of the delivery wire when the braided stent is in the partially implanted configuration pulls the recapture bump against the second expandable anchor to move the braided stent proximally while the puller bump and pusher bump are disengaged from the braided stent.

17. The system of claim 16 wherein the first expandable anchor is sized larger than a diameter of puller bump when the braided stent is in the partially implanted configuration.

18. The system of claim 16 wherein the first expandable anchor is sized to remain anchored independent of any movement of the puller bump when the braided stent is in the partially implanted configuration.

19. The system of claim 16 wherein the first expandable anchor is freed from the puller bump when the braided stent is in the partially implanted configuration.

* * * * *